(12) United States Patent
Corti et al.

(10) Patent No.: US 11,786,513 B2
(45) Date of Patent: Oct. 17, 2023

(54) COMPOSITIONS COMPRISING BERBERINE

(71) Applicant: INDENA S.P.A., Milan (IT)

(72) Inventors: Fabrizio Corti, Milan (IT); Massimo Ronchi, Milan (IT); Antonella Riva, Milan (IT)

(73) Assignee: INDENA S.P.A., Milan (IT)

( * ) Notice: Subject to any disclaimer, the term of this patent is extended or adjusted under 35 U.S.C. 154(b) by 247 days.

(21) Appl. No.: 16/966,298

(22) PCT Filed: Jan. 22, 2019

(86) PCT No.: PCT/IB2019/050511
§ 371 (c)(1),
(2) Date: Jul. 30, 2020

(87) PCT Pub. No.: WO2019/150225
PCT Pub. Date: Aug. 8, 2019

(65) Prior Publication Data
US 2020/0368215 A1 Nov. 26, 2020

(30) Foreign Application Priority Data
Feb. 2, 2018 (IT) .......... 102018000002333

(51) Int. Cl.
A61K 31/4375 (2006.01)
A61K 36/48 (2006.01)
A61K 36/752 (2006.01)
A61K 36/87 (2006.01)
A61K 47/14 (2017.01)

(52) U.S. Cl.
CPC .......... *A61K 31/4375* (2013.01); *A61K 36/48* (2013.01); *A61K 36/752* (2013.01); *A61K 36/87* (2013.01); *A61K 47/14* (2013.01)

(58) Field of Classification Search
None
See application file for complete search history.

(56) References Cited

U.S. PATENT DOCUMENTS

2013/0287708 A1 10/2013 Silberstein et al.
2016/0015813 A1 1/2016 Gokaraju et al.
2016/0235822 A1 8/2016 Holstein et al.

FOREIGN PATENT DOCUMENTS

| CN | 101606622 | 12/2009 |
|---|---|---|
| CN | 102949375 A | 3/2013 |
| CN | 102702190 | 4/2016 |
| EP | 0 348 781 | 1/1990 |
| EP | 2 149 377 | 2/2010 |
| EP | 3064200 A1 | 9/2016 |
| EP | 3118215 A1 | 1/2017 |
| JP | 2010-506576 A | 3/2010 |
| WO | 2007/017037 | 2/2007 |
| WO | 2010/055490 | 5/2010 |
| WO | 2015/136441 A1 | 9/2015 |

OTHER PUBLICATIONS

Chueshov et al., "Industrial technology of medicines," Ministry of Health of Ukraine, National Pharmaceutical Academy of Ukraine, vol. 2, Kharkov, 2002, pp. 352-355.
Minina et al., "Chemistry and technology of phytopreparations," GEOTAR—Media, Mosco, 2009. pp. 82-97.
Ponomarev, "Extraction of medicinal raw materials," Moscow, Medicine, 1976, pp. 115-120.
Pirillo et al., "Berberine, a plant alkaloid with lipid- and glucose-lowering properties: From in vitro evidence to clinical studies", Atherosclerosis, vol. 243, Issue 2, Dec. 2015, pp. 449-461.
Kumar et al., "Current knowledge and pharmacological profile of berberine: An update", European Journal of Pharmacology, 761(2015), pp. 288-297.
Dong et al., "Inhibition of PCSK9 Transcription by Berberine Involves Down-regulation of Hepatic HNF1α Protein Expression through the Ubiquitin-Proteasome Degradation Pathway", The Journal of Biological Chemistry, vol. 290, No. 7, Feb. 13, 2015, pp. 4047-4058.
Feng et al., "Transforming berberine into its intestine-absorbable form by the gut microbiota", Scientific Reports, 5:12155, Jul. 15, 2015, 15 pages.
Guo et al., "Berberine Ameliorates Hepatic Steatosis and Suppresses Liver and Adipose Tissue Inflammation in Mice with Diet-induced Obesity", Scientific Reports, 6:22612, Mar. 3, 2016, 11 pages.
Liu et al., "Research progress on berberine with a special focus on its oral bioavailability", Fitoterapia, vol. 109, 2016, pp. 274-282.
De Castro et al., "Effect of Grapefruit Juice, Naringin, Naringenin, and Bergamottin on the Intestinal Carrier-Mediated Transport of Talinolol in Rats" Journal of Agricultural and Food Chemistry, vol. 56, No. 12, 2008, pp. 4840-4845.
Zhao et al. "Grape Seed Procyanidin Reversal of P-glycoprotein Associated Multi-Drug Resistance via Down-regulation of NF-kB and MAPK/ERK Mediated YB-1 Activity in A2780/T Cells", PLOS ONE, vol. 8, Issue.8, e71071, Aug. 15, 2013, 11 pages.
International Search Report of the ISA for PCT/IB2019/050511 dated May 13, 2019, 2 pages.
Written Opinion of the ISA for PCT/IB2019/050511 dated May 13, 2019, 6 pages.
MadanapEla, "Shimbi Dhanya Guna," Key Attributes of TKDL, RS15/778, Traditional Knowledge Digital Library, 1998, 3 pages.
Ali Ibn-e-Abbas Majoosi, "Habbul Ameerbaarees," Key Attributes of TKDL, AH3/666, Traditional Knowledge Digital Library, 2005, 3 pages.
Nityanathasiddhah, "Pittaja Hrdroge Anupanam," Key Attributes of TKDL, VK5/782B, Traditional Knowledge Digital Library, 1986, 3 pages.
Priyavrata Sharma, "Daruharidra Guna Karma," Key Attributes of TKDL, VJ/246A, Traditional Knowledge Digital Library, 2004, 2 pages.

*Primary Examiner* — Michael Barker
(74) *Attorney, Agent, or Firm* — NIXON & VANDERHYE

(57) ABSTRACT

Disclosed are compositions including berberine combined with pea proteins and one or more surfactants. Also disclosed are processes for the preparation of the compositions, and the formulations and uses thereof.

18 Claims, 2 Drawing Sheets

_US 11,786,513 B2_

COMPOSITIONS COMPRISING BERBERINE

TECHNICAL FIELD OF INVENTION

The invention relates to compositions comprising berberine for the prevention and/or treatment of dyslipidaemia, hypercholesterolaemia, metabolic syndrome and cardiovascular disease.

PRIOR ART

Berberine (hereinafter called "BBR") is an alkaloid present in various plants, such as *Berberis aristata, Coptis chinensis* and *Hydrastis canadensis*, which are widely used in Chinese and Indian traditional medicine for their anti-parasitic, antibacterial and anti-inflammatory properties.

Numerous more recent studies have highlighted BBR's very broad spectrum of pharmacological activity, which suggests its possible clinical use in various therapeutic areas, including controlling metabolic syndrome. This latter application is particularly associated with the major antidyslipidaemic and hypoglycaemic effects observed at both preclinical and clinical levels [1,2].

The antidyslipidaemic and hypoglycaemic (post-prandial glycaemia) activity of BBR has been demonstrated in numerous clinical trials [1,2].

Important actions on the vascular wall and on the inflammatory mechanisms associated with cardiovascular complications in metabolic syndrome have also been observed [1,2].

The main mechanism whereby BBR exercises a protective effect in the atherosclerotic process is reduction of the LDL-C levels by inducing synthesis of the hepatic LDL-R receptors and inhibiting expression and secretion of the enzyme PCSK9 [3]. The latter mechanism currently represents a priority target for the development of the latest generation of antidyslipidaemia medicaments. Anti-PCSK9 monoclonal antibodies for the treatment of familial hypercholesterolaemia were recently launched, but have a very high therapeutic cost and significant side effects [2].

As regards the hypoglycaemic effects of BBR, a significant number of clinical publications demonstrate an improvement in the blood glucose parameters (associated with weight reduction) in patients with T2DM, or the metabolic parameters in patients with polycystic ovary syndrome.

The modulating activity of BBR on the cell energy regulation mechanism associated with the enzyme AMPk, which has become the most important and widely-studied target of blood glucose regulation, has also been demonstrated.

After oral administration, BBR is metabolised presystemically by the intestinal bacterial flora to form the main metabolite, berberrubine, which is then absorbed and reconverted to BBR in the liver, and excreted via the biliary route [4].

The liver therefore appears to be the main target organ of BBR from both the pharmacokinetic and the pharmacodynamic standpoints, because it reconverts the main absorbed metabolite, berberrubine, to BBR. LDL-R receptors (one of the main targets of BBR) are expressed in the liver cells; the liver plays an essential role in carbohydrate metabolism, and is the organ wherein BBR is conjugated and eliminated through the bile.

The hepatic activity of BBR has also proved significant in experimental models in vivo for the control of degenerative processes affecting the hepatic parenchyma, mainly steatosis associated with obesity induced by metabolic syndrome [5]. BBR therefore increasingly presents as a first-line product for metabolic syndrome, as it acts against several causes of the said syndrome, which has serious consequences for the health in general and cardiovascular risk in particular.

The main problem with using BBR is its very low oral absorption, which does not exceed 0.5% of the administered dose, only 0.36% of which reaches the systemic circulation [6]. This is due to several factors: poor intestinal absorption, elimination by the permeability glycoproteins (Pgp), presystemic metabolism by the bacterial flora, hepatic metabolism and biliary elimination. It is therefore necessary to administer large doses (500-2000 mg) several times a day, at the expense of patient compliance and adverse gastrointestinal effects. Numerous attempts have been made to increase the plasma levels of BBR, by means of formulation approaches or the use of specific Pgp inhibitors which eliminate BBRs from the enterocytes. In particular, it is known from the scientific literature that some plant extracts containing naringin from *Citrus* spp. [7] and procyanidins from grape seeds [8] inhibit Pgp activity.

European patent EP 2 149 377 [9] describes compositions comprising BBR or extracts comprising BBR combined with silymarin or with *Silybum marianum* extracts containing silymarin for the treatment of hyperglycaemia.

However, there is still a need to obtain formulations able to increase the oral bioavailability of BBR and improve its therapeutic index.

LIST OF FIGURES

SUMMARY OF THE INVENTION

Figure 1:
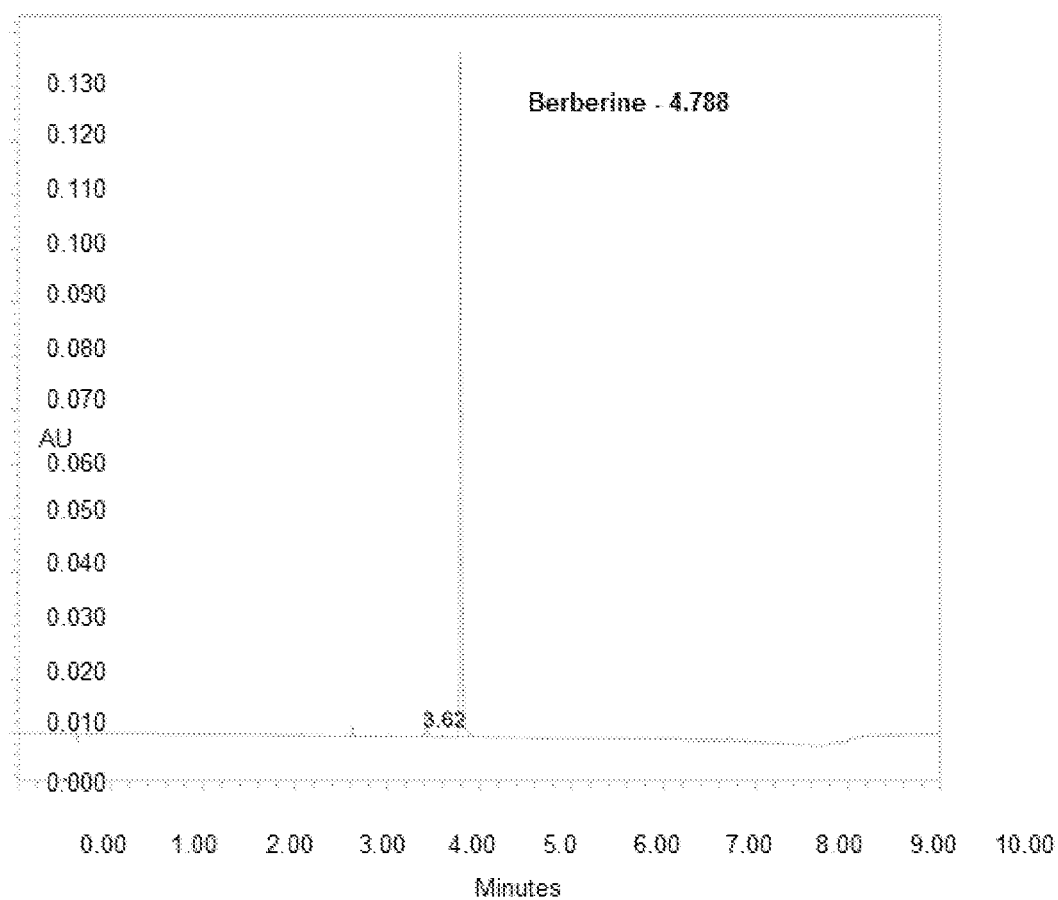
FIG. 1 shows the chromatogram of a sample of BBR combined with pea proteins and lecithin according to the invention (methanol solution, ~0.15 mg/ml).

The present invention relates to a composition comprising:
  a) berberine (BBR);
  b) pea proteins;
  c) one or more surfactants;
  and optionally
  d) a plant extract of the *Vitis* species or the *Citrus* species or combinations thereof.

The invention also relates to processes for the preparation of the composition, pharmaceutical or nutraceutical formulations comprising the composition, and the use of the composition for the prevention and/or treatment of dyslipidaemia, hypercholesterolaemia, metabolic syndrome and cardiovascular disease.

DETAILED DESCRIPTION OF THE INVENTION

It has been discovered that when BBR is combined with pea proteins in the presence of at least one surfactant, the solubility of BBR in aqueous solutions is greater than that of BBR alone. A further increase is observed when BBR is associated with pea proteins, a surfactant and an extract of the *Vitis* species, preferably a *Vitis vinifera* extract, and/or an extract of the *Citrus* species, preferably a *Citrus bergamia* extract. Without being bound by the theory, it is believed that the presence of at least one surfactant promotes a synergic interaction between BBR, pea proteins and *Vitis* and/or Citrus species extracts, if used, which in turn gives rise to an increase in the solubility and absorption of BBR.

In a first aspect thereof, the invention therefore relates to a composition comprising:
a) berberine (BBR);
b) pea proteins;
c) one or more surfactants;
and optionally
d) a plant extract of the *Vitis* species or the *Citrus* species or combinations thereof.

For the purposes of the present invention, BBR can be used in the form of an extract obtainable by aqueous extraction (aqueous extract) from the roots of *Berberis aristata, Coptis chinensis* or *Hydrastis canadensis*, more preferably an aqueous extract of *Berberis aristata* roots. The aqueous extract preferably has a BBR content ranging between 30 and 70% (w/w), more preferably 50% w/w. The extract can be obtained by conventional processes which comprise grinding the roots, extraction in an aqueous medium, precipitation and drying.

Even more preferably, BBR can be used in the form of an extract, hereinafter called "pure BBR", having a berberine content greater than 85% w/w, obtainable by further purification of a 50% w/w aqueous extract on a resin column.

BBR extracts and pure BBR which are also suitable for the embodiment of the invention are commercially available, for example from Indian Herbs Extractions.

The expression "pea proteins" identifies proteins obtained by a process of aqueous extraction from dried peas (*Pisum sativum*). They are commercially available, for example, from Roquette (France), under the trademark Nutralys®, and are characterised by high solubility (≥50%), high digestibility and a balanced amino-acid profile.

The expression "*Vitis* species extract" denotes one or more extracts of the *Vitis* species having a proanthocyanidin content greater than 90% by weight. A *Vitis vinifera* seed extract obtainable as described in WO 2007/017037 [10] or EP 0348781 [11], having a proanthocyanidin content equal to or greater than 95% by weight and a catechin and epicatechin content ≥5% by weight and ≤15% by weight, is preferably used. Said extract is commercially available from Indena S.p.A. under the trademark Enovita®.

The expression "*Citrus* species extract" denotes one or more extracts of the *Citrus* species having a flavanone content equal to or greater than 25% by weight. An extract of *Citrus bergamia* (bergamot orange extract) having a flavanone content greater than 28% by weight and a reduced furocoumarin (bergapten and bergamottin) content, obtainable as described in WO 2010/055490 [12], is preferably used.

The ratio between the extract containing BBR and the pea proteins preferably ranges between 1:1 w/w and 10:1 w/w, and more preferably amounts to 4:1 w/w, or the ratio between pure BBR and pea proteins ranges between 1:1 w/w and 10:1 w/w, and more preferably amounts to 3:1 w/w.

In the compositions according to the invention which contain, in addition to pea proteins, a *Vitis* species extract and/or a *Citrus* species extract, the weight ratio between the extract containing BBR or pure BBR and the total weight of the pea proteins and the *Vitis* species extract and/or the *Citrus* species extract ranges between 1:1 w/w and 5:1 w/w. The ratio between pea proteins and *Vitis* species extract and/or *Citrus* species extract ranges between 1:3 w/w and 3:1 w/w.

For the purposes of the present invention, the expression "surfactant" denotes one or more pharmacologically acceptable substances comprising a polar group (or head) and a non-polar group (or tail). Surfactants suitable for the preparation of the compositions according to the invention can be non-ionic, cationic, anionic or amphiphilic, and can be selected from those described in Remington: "The Science and Practice of Pharmacy", 22nd edition, Pharmaceutical Press, 2013. The surfactant is preferably selected from phospholipids, sucrose esters, polysorbates, polyoxyethylene castor oil derivatives, D-α-tocopheryl-polyethylene glycol succinate (Vitamin E TPGS), or mixtures thereof. More preferably, the surfactant is a lecithin, in particular phosphatidylcholine, phosphatidylserine, phosphatidyl ethanolamine or mixtures thereof; even more preferably, the lecithin is soya or sunflower lecithin. In the compositions according to the invention, the surfactant is present in amounts ranging between 5 and 30% w/w of the total weight of the BBR extract or pure BBR and pea proteins, and the *Vitis* species extract and/or the *Citrus* species extract, if used.

The compositions according to the invention preferably do not include silymarin or extracts of *Silybum marianum* containing silymarin.

The compositions according to the invention can contain other active ingredients of plant origin; however, in a preferred embodiment, the compositions consist of:
a) BBR;
b) pea proteins;
c) one or more surfactants;
and optionally
d) a plant extract of the *Vitis* species or the *Citrus* species or combinations thereof.

The compositions according to the invention can optionally contain pharmaceutically acceptable excipients suitable to obtain formulations for oral administration, such as tablets, capsules and granulates. Said excipients comprise, for example:
insoluble and soluble diluents, such as microcrystalline cellulose, calcium phosphate, calcium carbonate, mannitol, maltodextrins, isomalt or combinations thereof;
lubricants and/or glidants, such as silicon dioxide, talc, stearic acid, magnesium stearate or combinations thereof.

These and further excipients are described in Remington: "*The Science and Practice of Pharmacy*", 22nd edition, Pharmaceutical Press, 2013.

Typically, the formulations comprise a composition according to the invention, preferably in quantities ranging from 500 to 2000 mg, more preferably in quantities amounting to 500 mg, and at least one excipient. Typically, the weight ratio between the compositions according to the invention and the at least one excipient in the dosage form ranges between 1:5 and 5:1 w/w.

In a second aspect thereof, the invention relates to a process [process (P-1)] for obtaining the compositions and formulations according to the invention. These compositions and formulations can be obtained by adding BBR, pea proteins, and optionally a *Vitis* species extract or a *Citrus* species extract and/or excipients to a surfactant solution or dispersion. BBR, pea proteins, and optionally a *Vitis* species extract or a *Citrus* species extract and/or excipients can be added in successive steps, or in a single step.

A first preferred process [process (P-1)] comprises the following steps:
a-1) solubilise or disperse a surfactant or a mixture of surfactants in 50-100 volumes of an organic solvent preferably selected from ethyl alcohol, ethyl acetate and acetone until a solution or homogeneous dispersion is obtained;

b-1) add BBR, and optionally a *Vitis* species extract and/or a *Citrus* species extract, to the solution or dispersion obtained in step a-1), heating to a temperature preferably ranging between 40° C. and 70° C., more preferably 60° C., to obtain a dispersion;

c-1) cool the dispersion obtained in step b-1) to room temperature and add the pea proteins under stirring, preferably for about 10-15 minutes, until a dispersion is obtained;

d-1) optionally add a diluent, preferably microcrystalline cellulose, or a mixture of diluents, to the dispersion obtained in step c-1);

e-1) remove the solvent by low-pressure evaporation, preferably between 100 and 500 mbars, from the mixture obtained in step c-1), maintaining a temperature preferably ranging between 50° C. and 75° C., more preferably ≤65° C., optionally terminating the drying under vacuum in a stove set to a temperature of 60-65° C., until a solvent residue preferably <1.2% w/w is obtained;

f-1) calibrate the composition obtained at the end of step e-1) on a 10 mesh sieve and optionally add a lubricant and/or glidant preferably selected from stearic acid, magnesium stearate and silicon dioxide, preferably silicon dioxide.

A second preferred process [process (P-2)] comprises the following steps:

a-2) solubilise or disperse a surfactant or a mixture of surfactants in 5-10 volumes of an organic solvent preferably selected from ethyl alcohol, ethyl acetate and acetone, preferably ethyl alcohol, until a solution or homogeneous suspension is obtained;

b-2) separately from the solution or suspension obtained in step a-2), mix an extract containing BBR with pea proteins, optionally a *Vitis* species extract and/or a *Citrus* species extract, and a diluent, preferably microcrystalline cellulose, until a homogeneous mixture is obtained, typically for about 5 minutes;

c-2) add the mixture obtained in step b-2) to the solution or suspension obtained in step a-2) to obtain a mixture; keep the resulting mixture under stirring for about 10-15 minutes;

d-2) stove-dry the mixture obtained in step c-2) under vacuum at a temperature of about 60-65° C. until a residual solvent content of <1.2% w/w is obtained;

e-2) calibrate the composition obtained at the end of step d-2) on a 10-mesh sieve and optionally add one or more lubricants and/or glidants preferably selected from stearic acid, magnesium stearate and silicon dioxide, preferably silicon dioxide.

For the purposes of the present invention, the term "solution" indicates a liquid composition which appears clear on visual inspection; the term "dispersion" indicates a liquid composition which, on visual inspection, presents suspended particles and appears opaque and cloudy; the term "mixture" indicates a homogeneous mixture of solids and liquids other than a solution or dispersion, which presents as soft and malleable.

Moreover, for the avoidance of doubt, where numerical ranges are specified in the present description and claims, the extremes of the ranges shall be deemed to be included.

The synergic interaction between BBR, pea proteins and the optional *Vitis* species extract and/or *Citrus* species extract can be verified by means of solubility tests in simulated biological fluids, such as simulated gastric juice. The tests can be conducted by methods known to the skilled person, for example as reported in the experimental section below. The interaction is deemed to have taken place when an increase in solubility of at least approximately three times that obtained with uncombined BBR is observed. The solubility parameter is considered to be predictive of increased absorption.

In a further aspect thereof, the invention relates to the use of compositions (C) as a medicament, in particular for the prevention and/or treatment of dyslipidaemia, hypercholesterolaemia, metabolic syndrome and cardiovascular disease.

The examples set out in the experimental section below further illustrate the invention.

Experimental Section

Materials

The plant extract from *Berberis aristata* roots with a BBR content of about 50% and the pure BBR were obtained from Indian Herbs Extractions, Ramnagar.

The pea proteins were obtained from Roquette, France (Nutralys®).

The *Vitis vinifera* extract is commercially available from Indena S.p.A. under the trademark Enovita®, and is obtained by water-alcohol extraction, filtration, purification on resin column, and drying.

The *Citrus bergamia* (bergamot orange) extract was obtained from H&AD Herbal and Antioxidant Derivatives.

The soya lecithin was obtained from Cargill®.

The percentages of the ingredients in the compositions according to the examples are expressed by weight, as a ratio of the total weight of the composition.

PREPARATION EXAMPLES

Example 1—Composition Containing BBR Extract Titrated to 50% w/w, Pea Proteins and Lecithin

| | |
|---|---|
| 50% w/w BBR extract | 60.0% |
| Pea proteins | 15.0% |
| Lecithin | 14.0% |
| Hydroxypropylcellulose | 5.0% |
| Silicon dioxide | 2.0% |
| Polysorbate 80 | 4.0% |

The composition was obtained by following process (P-1), comprising the following steps.

1. Polysorbate 80 and hydroxypropylcellulose were dissolved in ethyl alcohol until a solution was obtained.

2. BBR extract titrated to 50% w/w was added to the solution obtained in step 1, under magnetic stirring, and heated to 60° C. until a dispersion was obtained.

3. Lecithin was added under magnetic stirring to the dispersion obtained in step 2, and heated to 60° C.

4. The dispersion obtained in step 3 was cooled to room temperature, and the pea proteins were added to obtain a dispersion.

5. The solvent was removed by low-pressure evaporation from the dispersion obtained in step 4, maintaining the temperature at <65° C.

6. The product obtained in step 5 was stove-dried under vacuum at 65° C. until the ethyl alcohol residue was <1.2%.

7. The product obtained in step 6 was calibrated on a 10-mesh sieve, and silicon dioxide pre-sieved through a 50-mesh sieve was added.

Example 2—Composition Containing BBR Extract Titrated to 50% w/w, Pea Proteins, Lecithin and *Citrus bergamia* Extract

| | |
|---|---|
| BBR extract titrated to 50% w/w | 54.6% |
| Pea proteins | 13.2% |
| Lecithin | 12.7% |
| *Citrus bergamia* extract | 9.1% |
| Hydroxypropylcellulose | 5.0% |
| Silicon dioxide | 1.8% |
| Polysorbate 80 | 3.6% |

The composition was obtained by following the process described in Example 1, with the difference that *Citrus bergamia* extract was also added in step 2.

Example 3—Composition Containing 50% w/w BBR Extract, Pea Proteins, Lecithin and *Vitis vinifera* Seed Extract

| | |
|---|---|
| 50% w/w BBR extract | 54.6% |
| Pea proteins | 13.2% |
| Lecithin | 12.7% |
| *Vitis vinifera* seed extract | 9.1% |
| Hydroxypropylcellulose | 5.0% |
| Silicon dioxide | 1.8% |
| Polysorbate 80 | 3.6% |

The composition was obtained by following the process described in Example 1, with the difference that *Vitis vinifera* seed extract was also added in step 2.

Example 4—Coated Tablets

| | |
|---|---|
| Composition of Example 1 | 500.0 mg |
| Dicalcium phosphate dihydrate | 200.0 mg |
| Mannitol | 150.0 mg |
| Polyvinylpolypyrrolidone | 30.0 mg |
| Magnesium stearate | 10.0 mg |
| Colloidal silicon dioxide | 10.0 mg |
| Hydroxypropyl methylcellulose-based coating | 20.0 mg |

Example 5—Rigid Gelatin Capsules

| | |
|---|---|
| Composition of Example 3 | 550.0 mg |
| Microcrystalline cellulose | 60.0 mg |
| Magnesium stearate | 10.0 mg |
| Colloidal silicon dioxide | 10.0 mg |

Example 6—Water-Dispersible Granulate

| | |
|---|---|
| Composition of Example 2 | 550.0 mg |
| Maltodextrin | 1200.0 mg |
| Fructose | 425.0 mg |
| Guar gum | 200.0 mg |
| Orange flavouring | 100.0 mg |
| Sucralose | 20.0 mg |
| Colloidal silicon dioxide | 5.0 mg |

Assays

Solubility Test in Simulated Biological Fluids

The solubility test was conducted by comparing samples containing equal amounts of BBR.

The compositions prepared as described in Examples 1, 2 and 3 were assayed by comparison with pure BBR (Reference 1) and with a composition containing 33% BBR extract titrated to 50% w/w, 65% lecithin and 2% silicon dioxide (Reference 2), but without pea proteins, to evaluate the increased solubility in simulated biological fluids.

The analysis was conducted by the UPLC (Ultra High Performance Liquid Chromatography) method described below:

APPARATUS: Waters® Acquity UPLC® H-Class System.

Empower software (Empower System Enterprise Client/Server).

COLUMN: Stationary phase: Acquity UPLC® CSH™ C18; Dimensions: 1=100 mm; I.D.=2.1 mm; particle size: 1.7 µm; Manufacturer: Waters.

MOBILE PHASE: Solvent A: 0.5% phosphoric acid (w/v); Solvent B: acetonitrile.

LINEAR GRADIENT

TABLE 1

| Time (min) | Solvent A* (%) | Solvent B (%) |
|---|---|---|
| 0.0 | 95 | 5 |
| 6.0 | 50 | 50 |
| 6.5 | 0 | 100 |
| 7.5 | 0 | 100 |
| 8.0 | 95 | 5 |
| 10.0 | 95 | 5 |

*The percentages of solvents A and B are expressed by volume compared with the total.

ANALYSIS CONDITIONS: Flow rate: 0.4 ml/minute; Detection: 348 nm.

SOLUBILISATION SOLVENT: 80% methanol

BLANK SOLUTION: 80% methanol

SAMPLE SOLUTION: 30 mg in 200 ml (Chromatogram of a typical sample of ~0.15 mg/ml, in FIG. 1).

Figure 2:
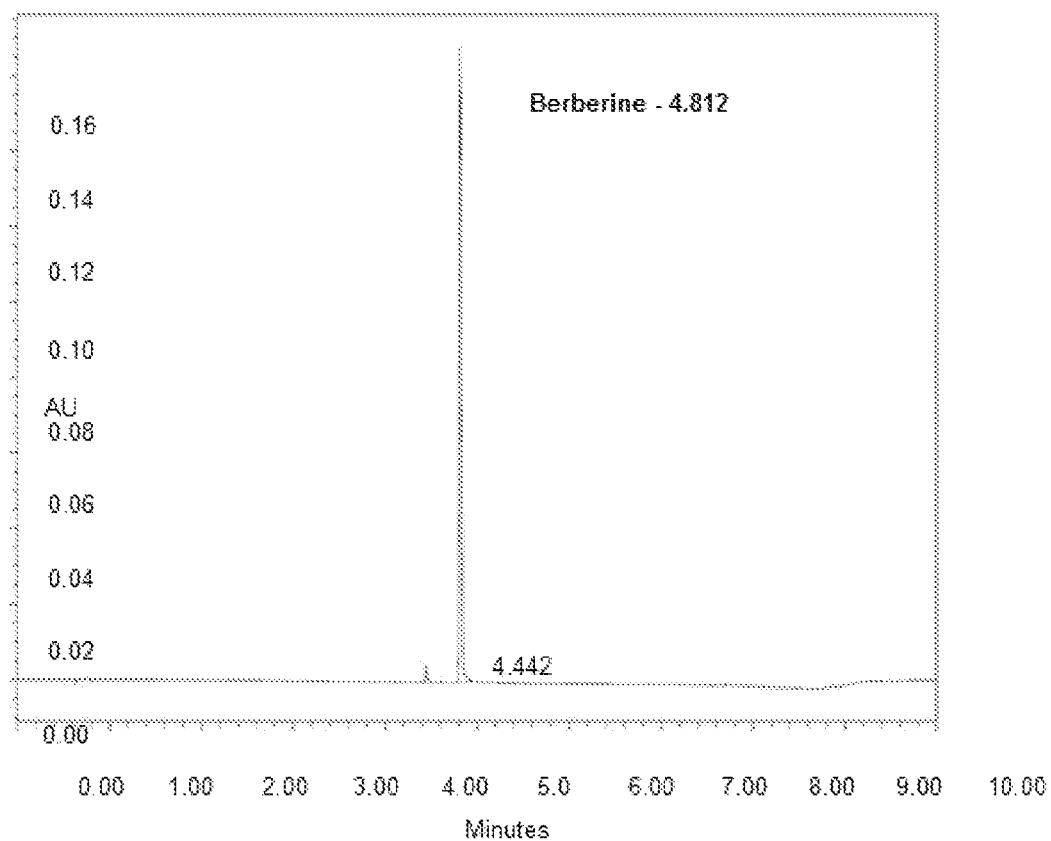
FIG. 2 shows the chromatogram of a standard solution of BBR chloride (methanol solution, ~0.05 mg/ml).

STANDARD SOLUTION: 10 mg of pure reference BBR in 200 ml of methanol (Standard solution ~0.05 mg/ml, typical chromatogram in FIG. 2).

The solubility test was conducted using Fasted-State Simulated Gastric Fluid (FaSSGF), prepared as reported below, as solvent.

1) Preparation of an NaCl/HCl solution for FaSSGF (1 litre):

2 g of NaCl was dissolved in 0.9 l of purified water, the pH was adjusted to 1.6 with HCl, and the mixture was made up to volume with purified water (1 litre).

2) 0.06 g of powder* (FaSSGF—Biorelevant media) was added to about 500 ml of the NaCl/HCl solution at room temperature and made up to volume (1 l) with the NaCl/HCl solution to obtain a clear, ready-for-use liquid.

*Final sodium taurocholate 0.08 mM, final lecithin 0.02 mM

Table 2 below shows the test results:

TABLE 2

| Sample | Description | FASSGF solubility (mg/ml) |
|---|---|---|
| Reference 1 | pure BBR | 0.113 |
| Reference 2 | BBR extract titrated to 50% w/w + lecithin | 0.281 |

TABLE 2-continued

| Sample | Description | FASSGF solubility (mg/ml) |
|---|---|---|
| Example 1 | BBR extract titrated to 50% w/w + pea proteins + lecithin | 0.321 |
| Example 2 | BBR extract titrated to 50% w/w + pea proteins + lecithin + *Citrus bergamia* extract | 0.396 |
| Example 3 | BBR extract titrated to 50% w/w + pea proteins + lecithin + *Vitis vinifera* seed extract | 0.397 |

The results set out in Table 2 indicate that the compositions according to the invention exhibit greater solubility in simulated gastric juice than pure BBR, whether used alone or combined with lecithin only. The addition of pea proteins clearly gives rise to a further increase in solubility. The addition of a *Citrus bergamia* extract or a *Vitis vinifera* seed extract gives rise to a further increase in the solubility of BBR. In particular, the solubility of BBR increases about three-fold when BBR is combined with pea proteins and lecithin only, but about four-fold when it is also combined with a *Citrus bergamia* extract or a *Vitis vinifera* seed extract. These findings demonstrate that the compositions according to the invention increase the solubility of BBR in an aqueous medium, which constitutes the greatest obstacle to its intestinal absorption.

Comparative evaluation of the bioavailability and impact on the intestinal mucosa of reference compositions containing BBR extract and lecithin only, and compositions containing BBR according to the invention (BBR as described in Example 3)

The absorption and bioavailability of BBR were determined with an in vitro model of human intestinal epithelium based on Caco-2 human intestinal adenocarcinoma cells (ATCC, HTB-37TM), organised as a functional monolayer on Transwell® inserts. Transwell® inserts are characterised by two compartments, apical (or luminal) and basolateral (or serosal), separated by a microporous membrane.

To determine the potential involvement in BBR absorption of glycoprotein-P (P-gp), a membrane pump that expels a wide range of substrates absorbed by the enterocytes into the intestinal lumen, the in vitro absorption experiments were conducted in the presence of Verapamile, a selective glycoprotein-P (P-gp) inhibitor.

Before the in vitro absorption test was conducted, a dose of composition consisting of BBR extract titrated to 50% w/w and lecithin (Reference 2), and a dose of the composition of Example 3, were exposed for three hours to an in vitro digestive process simulating physiological digestion. The two digested formulations were then added to the apical compartment of the intestinal epithelium in vitro to conduct the absorption test. As shown in Table 3, the absorption of BBR from the composition of Example 3 is significantly greater than that of BBR from the composition of Reference 2.

TABLE 3

| | Absorption (µM) |
|---|---|
| Reference 2 | 0.65 ± 0.06 |
| Composition of Example 3 | 1.20 ± 0.12 |

After exposure to the digested formulations, the cell viability of the intestinal epithelium model was evaluated with an MTS assay based on reduction of the MTS tetrazole compound by the viable cells to generate the coloured product formazan, quantifiable by measuring absorbance at 490 nm. The dose (concentration (mg/ml))-response (% viability of intestinal epithelium) values obtained are set out in Tables 4 and 5 below:

TABLE 4

Reference 2

| BBR concentration (mg/mL) | Viability of intestinal epithelium | Standard deviation |
|---|---|---|
| 8.2 | 53.44599 | 0.20693 |
| 4.1 | 83.86349 | 1.40695 |
| 2.1 | 93.30683 | 1.41046 |
| 1.4 | 98.47581 | 1.25868 |
| 1 | 111.1332 | 0.94825 |

TABLE 5

Composition of Example 3

| BBR concentration (mg/mL) | Viability of intestinal epithelium | Standard deviation |
|---|---|---|
| 8.2 | 78.13688 | 1.62526 |
| 4.1 | 103.3904 | 3.63005 |
| 2.1 | 100.7605 | 1.18853 |
| 1.4 | 107.5412 | 3.70722 |
| 1 | 109.8226 | 1.24303 |

The dose-response values obtained demonstrate that, at the maximum concentration of BBR (8.2 mg/mL), Reference 2 induces a 46.6% reduction in the viability of intestinal epithelium, significantly greater than that induced by the composition of Example 3 (21.9%).

This indicates that the compositions according to the invention, in particular the composition according to Example 3, unlike the extract not combined with pea proteins, guarantee greater bioaccessibility of the active ingredient BBR in the presence of the P-gp inhibitor Verapamile, confirming the importance of this cell mechanism in the low intestinal absorption of BBR.

Moreover, BBR concentration being equal, the composition according to Example 3 proved safer than Reference 2, as indicated by the greater viability of the intestinal mucosa, thus surprisingly ensuring, despite the increased absorption, a lower potential impact on the gastrointestinal disorders typical of BBR.

Pharmacokinetics Test in the Rat

A pharmacokinetics test was conducted on rats to evaluate the increased absorption obtainable using the composition described in Example 1.

The test was conducted by orally administering 1000 mg/kg of composition according to Example 1, equivalent to 100 mg/kg of pure BBR, to three Sprague Dawley rats, and 100 mg/kg of pure BBR to three rats. The products were administered in distilled water with 1% by weight of methylcellulose as solubiliser. Blood samples were then taken from the retroocular sinus amounting to a volume of 0.5 ml in heparinised test tubes after 15 min, 30 min, 1 h, 2 h, 4 h and 6 h.

The samples thus obtained were analysed after extraction and treatment with glucuronidase and arylsulphatase by a standard HPLC method, coupled with a mass/mass spectrometry detector.

An approximately six-fold increase in the maximum plasma levels of BBR compared with those obtained after administration of a BBR extract in equimolar doses was unexpectedly found.

An approximately three-fold increase was observed compared with the areas under the curve (AUC) representative of the total absorption of the compound.

These data demonstrate the predictive value of the solubility test, and confirm the improvement in the pharmacokinetic parameters and bioavailability in vivo.

REFERENCES

1) Alberico Luigi Catapano, Berberine, a plant alkaloid with lipid- and glucose-lowering properties: From in vitro evidence to clinical studies Atherosclerosis Volume 243, Issue 2, December 2015, Pages 449-461.
2) Anil Kumar, Current knowledge and pharmacological profile of berberine: An update European Journal of Pharmacology 761(2015)288-297.
3) Jin~lwen Liu, Inhibition of PCSK9 Transcription by Berberine Involves Down-regulation of Hepatic HNF1 a Protein Expression through the Ubiquitin-Proteasome Degradation Pathway The Journal of Biological Chemistry vol. 290, no. 7, pp. 4047-4058, 13, 2015.
4) Jian-Dong Jiang, Transforming berberine into its intestine-absorbable form by the gut Microbiota Scientific Reports |5:12155|DOI: 10.1038/srep12155 2015).
5) Ting Guo, Berberine Ameliorates Hepatic Steatosis and Suppresses Liver and Adipose Tissue Inflammation in Mice with Diet-induced Obesity Scientific Reports 6: 22612 (2016).
6) Xiao-Ying Long, Research progress on berberine with a special focus on its oral bioavailability Fitoterapia 109 (2016) 274-282.
7) De Castro, Whocely Victor, et al. "Effect of grapefruit juice, naringin, naringenin, and bergamottin on the intestinal carrier-mediated transport of talinolol in rats." Journal of agricultural and food chemistry 56.12 (2008): 4840-4845.
8) Zhao, Bo-xin, et al. "Grape seed procyanidin reversal of p-glycoprotein associated multi-drug resistance via down-regulation of NF-κB and MAPK/ERK mediated YB-1 activity in A2780/T cells." PloS one 8.8 (2013): e71071.
9) EP 2 149 377 (Velleja Research SRL) published on Mar. 2, 2010 and granted on 14/09/2016.
10) WO 2007/017037 (A1) (Indena S.p.A.) published on 15/02/2007.
11) EP 0348781 (TECNOFARMACI S.p.A. and INDENA S.p.A.), published on Mar. 1, 1990 and granted on 30/09/1992.
12) WO 2010/055490 (A1) (Herbal & Antioxidant Derivatives S.r.L.), published on 20/05/2010.

The invention claimed is:

1. A composition comprising:
    a) berberine (BBR) in the form of an extract;
    b) pea proteins;
    c) one or more surfactants; and
    d) a plant extract of the *Vitis* or *Citrus* species or combinations thereof,
    wherein the extract containing BBR and the pea proteins are present in a ratio from 1:1 w/w to 10:1 w/w, and
    wherein said one or more surfactants comprises a lecithin.

2. The composition according to claim 1, wherein berberine is used in the form of an aqueous extract of *Berberis aristata*, *Coptis chinensis* or *Hydrastis canadensis* roots.

3. The composition according to claim 2, wherein the aqueous extract is obtained from *Berberis aristata* roots.

4. The composition according to claim 2, wherein the extract contains a quantity of berberine ranging from 30% w/w to 70% w/w.

5. The composition according to claim 4, wherein the extract contains a quantity of berberine equal to 50% w/w.

6. The composition according to claim 1, wherein berberine is used in the form of an extract having a berberine content greater than 85% w/w.

7. The composition according to claim 1, wherein the surfactant is selected from phospholipids, sucrose esters, polysorbates, polyoxyethylene castor oil, D-α-tocopherylpolyethyleneglycol succinate or mixtures thereof.

8. The composition according to claim 1, wherein the lecithin is soy lecithin or sunflower lecithin.

9. The composition according to claim 1, comprising a *Vitis vinifera* seed extract or a *Citrus bergamia* extract or combinations thereof.

10. Process for the preparation of a composition according to claim 1, said process comprising preparing a solution or dispersion of a surfactant, and adding, in one or more successive steps, BBR, pea proteins, an extract of the *Vitis* species and/or an extract of the *Citrus* species.

11. A composition or formulation obtainable by the process of claim 10.

12. A formulation comprising a composition according to claim 1, and at least one suitable pharmaceutically acceptable excipient.

13. A composition comprising:
    a) berberine (BBR);
    b) pea proteins; and
    c) one or more surfactants,
    wherein said one or more surfactants comprises a lecithin, and
    wherein BBR and the pea proteins are present in a ratio from 1:1 w/w to 10:1 w/w.

14. The composition according to claim 3, wherein the extract contains a quantity of berberine ranging from 30% w/w to 70% w/w.

15. The composition according to claim 2, wherein the surfactant is selected from phospholipids, sucrose esters, polysorbates, polyoxyethylene castor oil, D-α-tocopherylpolyethyleneglycol succinate or mixtures thereof.

16. The composition according to claim 3, wherein the surfactant is selected from phospholipids, sucrose esters, polysorbates, polyoxyethylene castor oil, D-α-tocopherylpolyethyleneglycol succinate or mixtures thereof.

17. Process for the preparation of a composition according to claim 13, said process comprising preparing a solution or dispersion of a surfactant, and adding, in one or more successive steps, BBR and pea proteins.

18. A composition comprising:
    a) berberine (BBR);
    b) pea proteins;
    c) one or more surfactants; and
    d) a plant extract of the *Vitis* or *Citrus* species or combinations thereof,
    obtainable by a process comprising:
        preparing a solution or dispersion of one or more surfactants; and
        adding to the solution or dispersion, in one or more successive steps, BBR, pea proteins, an extract of the *Vitis* species or an extract of the *Citrus* species,
    wherein said one or more surfactants comprises a lecithin, and wherein BBR and the pea proteins are present in a ratio from 1:1 w/w to 10:1 w/w.

* * * * *